US00PP21743P2

(12) United States Plant Patent
Yencho et al.

(10) Patent No.: US PP21,743 P2
(45) Date of Patent: Mar. 1, 2011

(54) SWEETPOTATO PLANT NAMED 'NCORNSP-011MNLC'

(50) Latin Name: ***Ipomoea batatas* (L.) Lam.**
Varietal Denomination: NCORNSP-011MNLC

(75) Inventors: G. Craig Yencho, Raleigh, NC (US); Kenneth V. Pecota, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/590,492

(22) Filed: Nov. 9, 2009

(51) Int. Cl.
*A01H 5/00* (2006.01)

(52) U.S. Cl. ..... Plt./258
(58) Field of Classification Search ..... Plt./258, Plt./395, 373
See application file for complete search history.

*Primary Examiner*—Annette H Para
(74) *Attorney, Agent, or Firm*—Jondle & Associates, P.C.

(57) ABSTRACT

'NCORNSP-011MNLC' is a new and distinct variety of ornamental sweetpotato having a very compact, semi-upright, densely-mounding cultivar producing many, short shoots; the instant variety is distinguishable from other cultivars by its purple leaves that have 5 to 7 extremely deep lobes, a very compact habit and erect architecture; and 'NCORNSP-011MNLC' has a good vigor, very well-branched, well-suited for production as a landscape or containerized plant and the production of flowers is rare, even under short day conditions.

3 Drawing Sheets

Latin name of the genus and species: *Ipomoea batatas* (L.) Lam.

Variety denomination: 'NCORNSP-011MNLC'.

BACKGROUND OF THE INVENTION

*Ipomoea batatas* is a member of the morning glory family Convolvulaceae. The cultivated members of *Ipomoea batatas* are commonly produced for consumption of their enlarged storage roots and they are commonly referred to as the white or yellow sweetpotato and the orange yam. The plants of the edible sweetpotato types are typically fast-growing, green vines possessing a wide variety of leaf shapes ranging from palmate and deeply lobed, to cordate or triangular shaped leaves with no lobes. Ornamental sweetpotatoes, which have been bred and selected for their unique foliage colors, leaf shapes, and plant habits, typically do not produce large fleshy storage roots like the sweetpotato cultivated for consumption. The storage roots produced by ornamental sweetpotatoes are typically not as large because no selection has been exercised for yield, thus storage roots do not begin to swell until very late in the season and those that are produced are not very attractive.

Like their cultivated forms, ornamental sweetpotato plants are a heat loving, drought tolerant vine grown as an annual, but they possess unique foliage colors, leaf shapes, and growth habits, which have significant value in the ornamental marketplace. They are highly desirable in the landscape and ornamental industries because their foliage comes in a wide variety of colors and shapes. Also, they can be grown in a potted plant and/or mixed planting format, and they have the ability to cover a large space or hang over walls and pots creating brightly colored and textured backdrops in gardens and patios. Most ornamental sweetpotatoes grow and last the entire growing season and they require little maintenance. Moreover, these plants have few insect or disease problems.

Until the release of the Sweet Caroline series of ornamental sweetpotatoes (see below) there were six popular types of ornamental sweetpotatoes, cultivated primarily as annual, summer vines in landscaping applications. These six cultivars are: 'Blackie' (unpatented), having purple foliage and lavender flowers; 'Terrace Lime' (unpatented) and 'Margarita' (unpatented; also known as 'Sulfur'), which have large brilliant chartreuse leaves and lavender blooms; 'Black Heart' (unpatented; also known as 'Ace of Spades'), having heart-shaped leaves with burgundy purple color; 'Tricolor' (unpatented; also known as 'Pink Frost'), a variegated plant having pale green, white, and pink-margined leaves; and 'Lady Fingers' (unpatented), which has medium green, dainty leaves divided into long, thin, finger-like lobes which are complemented by burgundy stems and veins.

To meet the growing horticultural demand for ornamental sweetpotatoes it is desirable to produce new cultivars of ornamental sweetpotato with attractive foliage colors, leaf shapes, and plant architectures. In addition, it would be advantageous to develop cultivars of ornamental sweetpotato exhibiting a more compact growth, and which do not out-compete other species in mixed containers.

'NCORNSP-011MNLC' was bred to meet the increasing demand for new ornamental sweetpotatoes and this plant patent application describes this new and distinct invention. 'NCORNSP-011MNLC' is a very compact, semi-upright, densely-mounding plant producing many short shoots. It is distinguishable from other cultivars by its dark purple leaves that have 5-7 extremely deep lobes, a very compact habit and erect mounding plant architecture. The extremely deep-lobed feature of the leaves of this plant and the plant architecture is what makes 'NCORNSP-011MNLC' unique amongst the current ornamental sweetpotatoes in the marketplace. 'NCORNSP-011MNLC' also exhibits very good vigor and is very well-branched.

In greenhouse and field trials conducted since 2005 by the breeding program and industry collaborators 'NCORNSP-011MNLC' has been shown to be much less vigorous than *Ipomoea batatas* 'Margarita' and 'Blackie' and is suitable for use as a landscape or containerized plant. The production of flowers by 'NCORNSP-011MNLC' is rare even under short day conditions.

'NCORNSP-011MNLC' originated from open-pollinated seed harvested from the breeding clone 'NC1650-009N' (the female parent; unpatented). These botanical seed were harvested from our winter greenhouse crossing blocks between September of 2003 and April of 2004 in North Carolina. Botanical seed from this half-sib family were planted in the greenhouse during the spring of 2005. The first cycle of selection on the population was exercised in the seedling trays and survivors were transferred to a single 6-inch pot, which was then maintained in the greenhouse. Cuttings (2 each) were taken from the plants in April and planted at a research station in North Carolina as 2-plant un-replicated plots during late June to early July 2005. A single, individual clone, now known as 'NCORNSP-011MNLC' was selected Sep. 1, 2005 because of its combination of exceptional ornamental sweetpotato features, and has been propagated asexually since that time.

Since its selection, *Ipomoea batatas* 'NCORNSP-01MNLC' has been asexually reproduced at a greenhouse in North Carolina predominantly by vegetative propagation of vine cuttings. Successively, there have been four cycles of vegetative propagation, one cycle of tissue culture micro propagation, and multiple vegetative propagation cycles to increase the plant population. Asexual reproduction of 'NCORNSP-01MNLC' by vine cuttings has shown that the unique features of the new cultivar are stable and the plant reproduces true to type in successive generations of asexual reproduction.

REFERENCE TO PLANT BREEDERS RIGHTS

Plant Breeders Rights for 'NCORNSP-011MNLC' have been applied for in Canada in October 2009. 'NCORNSP-011MNLC' has not been made publicly available or sold more than one year prior to the date of this application.

SUMMARY OF THE INVENTION

'NCORNSP-011MNLC' is a very compact, semi-upright, densely-mounding plant producing many short shoots. It is distinguishable from other cultivars by its dark purple leaves that have 5-7 extremely deeply lobed leaves, a very compact habit and erect mounding plant architecture. The extremely deep-lobed feature of the leaves of this plant and the plant architecture is what makes 'NCORNSP-011MNLC' unique amongst the current ornamental sweetpotatoes in the marketplace. 'NCORNSP-011MNLC' also exhibits very good vigor and is very well branched. It is less vigorous than *Ipomoea batatas* 'Margarita' and 'Blackie' and is well suited for production as a landscape or containerized plant. The production of flowers by 'NCORNSP-011MNLC' is rare even under short day conditions.

BRIEF DESCRIPTION OF THE PHOTOGRAPHS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*. Photos were taken in summer 2009 in North Carolina, under natural light.

DESCRIPTION OF THE NEW VARIETY

The following is a detailed description of the botanical characteristics of a new and distinct variety of *Ipomoea batatas* plant known by the variety name *Ipomoea batatas* 'NCORNSP-011MNLC'. All colors cited herein refer to The Royal Horticultural Society Colour Chart (The Royal Horticultural Society, London, 1995, $4^{th}$ ed.) designations except where general terms of ordinary dictionary significance are used. Where dimensions, sizes, colors, and other characteristics are given, it is to be understood that such characteristics are approximations or averages set forth as accurately as practicable.

The descriptions reported herein are from 68-day-old specimens grown individually in six-inch "azalea" pots. The plants were grown in Raleigh, N.C., under commercial practice in a glass-covered greenhouse where, during the spring, day and night temperatures range between 18-30° C. and 15-21° C., respectively. Plant descriptions were taken in June 2009. *Ipomoea batatas* 'NCORNSP-011MNLC' has not been observed under all possible environmental conditions; therefore, the phenotype may vary with variations in the environment such as season, temperature, light intensity, day length, cultural conditions, and the like.

DETAILED BOTANICAL DESCRIPTION

Classification:

*Botanical name.*—*Ipomoea batatas* (L.) Lam.

*Common name.*—Sweetpotato.

*Variety name.*—'NCORNSP-011MNLC'.

Growth conditions: 'NCORNSP-011MNLC' has excellent vigor, has a rapid growth rate, and is very adaptable to container culture. In locales with mild winter conditions, 'NCORNSP-011MNLC' will grow perennially; otherwise it is an annual plant. Similar to cultivated sweetpotatoes, wind or rain rarely causes much damage to 'NCORNSP-011MNLC', but if damage does occur, the plant drops the damaged leaves and grows new shoots at nodes where the leaves were lost. Under low light levels in a greenhouse, 'NCORNSP-011MNLC' can develop intumescence, which will remain on the affected foliage, but will be outgrown with new foliage.

Figure 1:
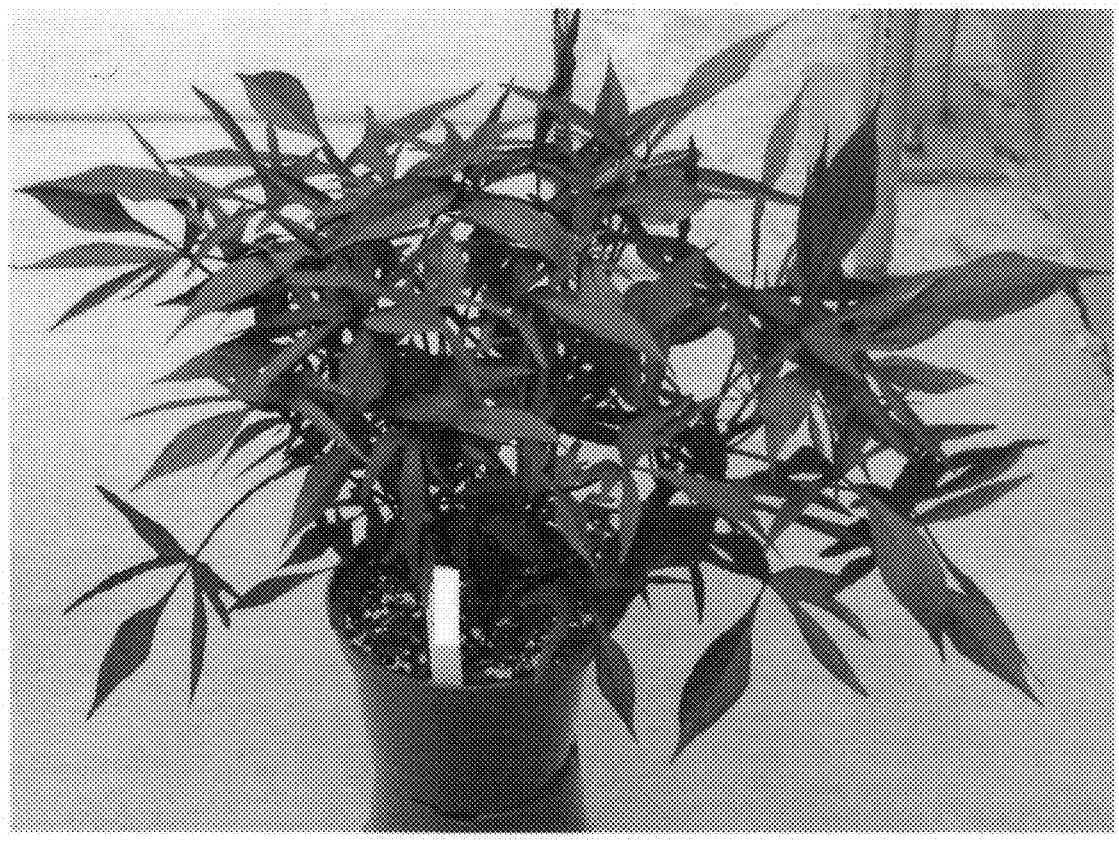
FIG. 1 shows a typical specimen of greenhouse-grown *Ipomoea batatas* 'NCORNSP-011MNLC' from the side, 81 days after planting.
Figure 2:
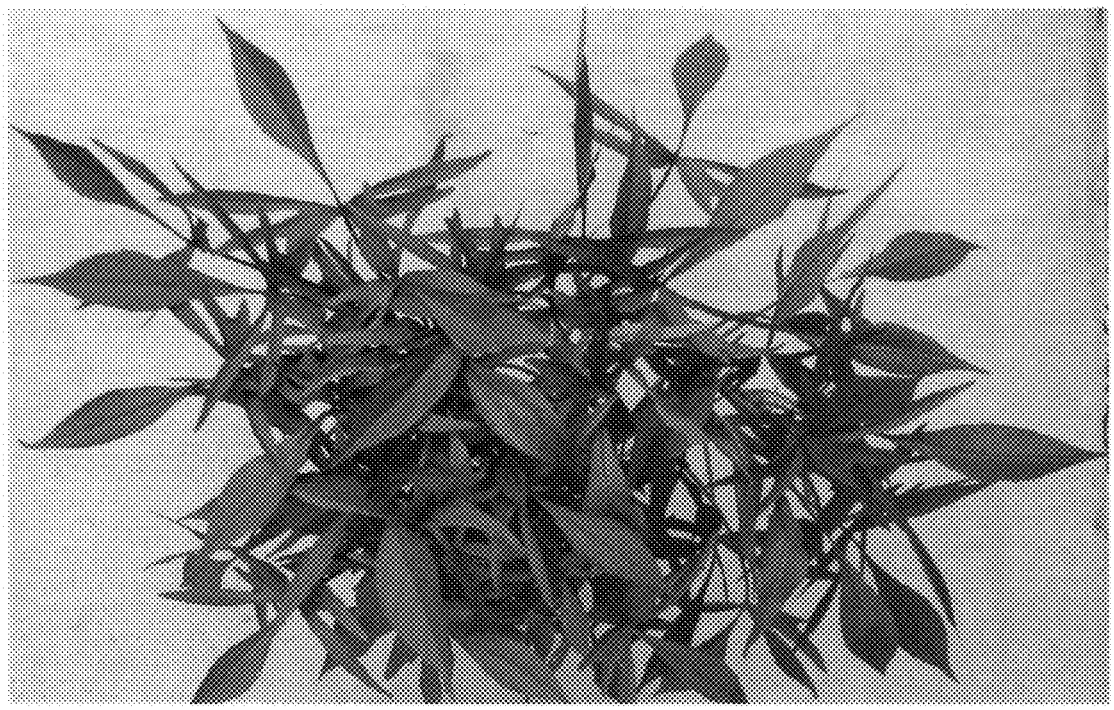
FIG. 2 shows a typical specimen of greenhouse-grown *Ipomoea batatas* 'NCORNSP-011MNLC' from the top, 81 days after planting.
Figure 3:
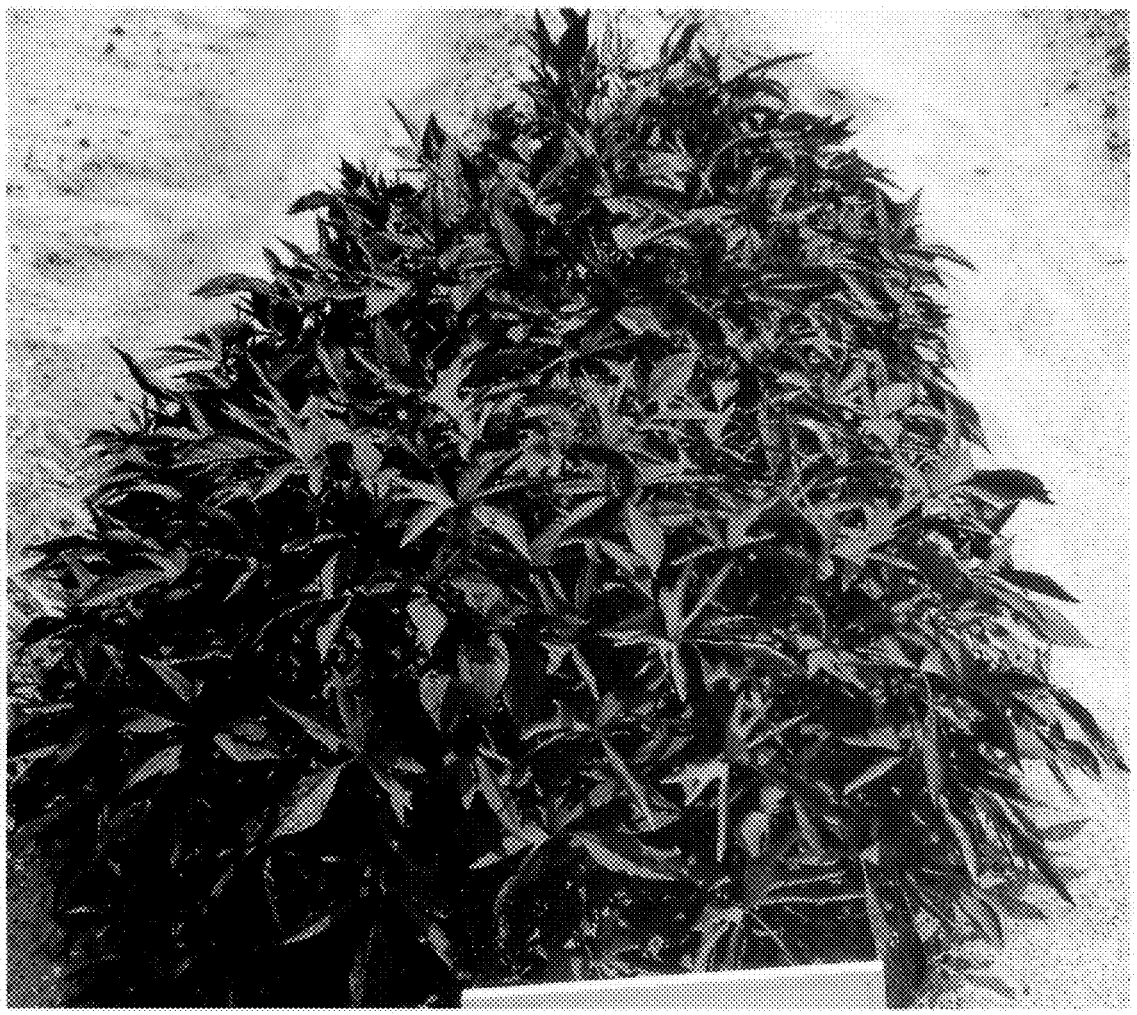
FIG. 3 shows a typical specimen of *Ipomoea batatas* 'NCORNSP-011MNLC' from the side in the field, 59 days after planting.
Figure 4:
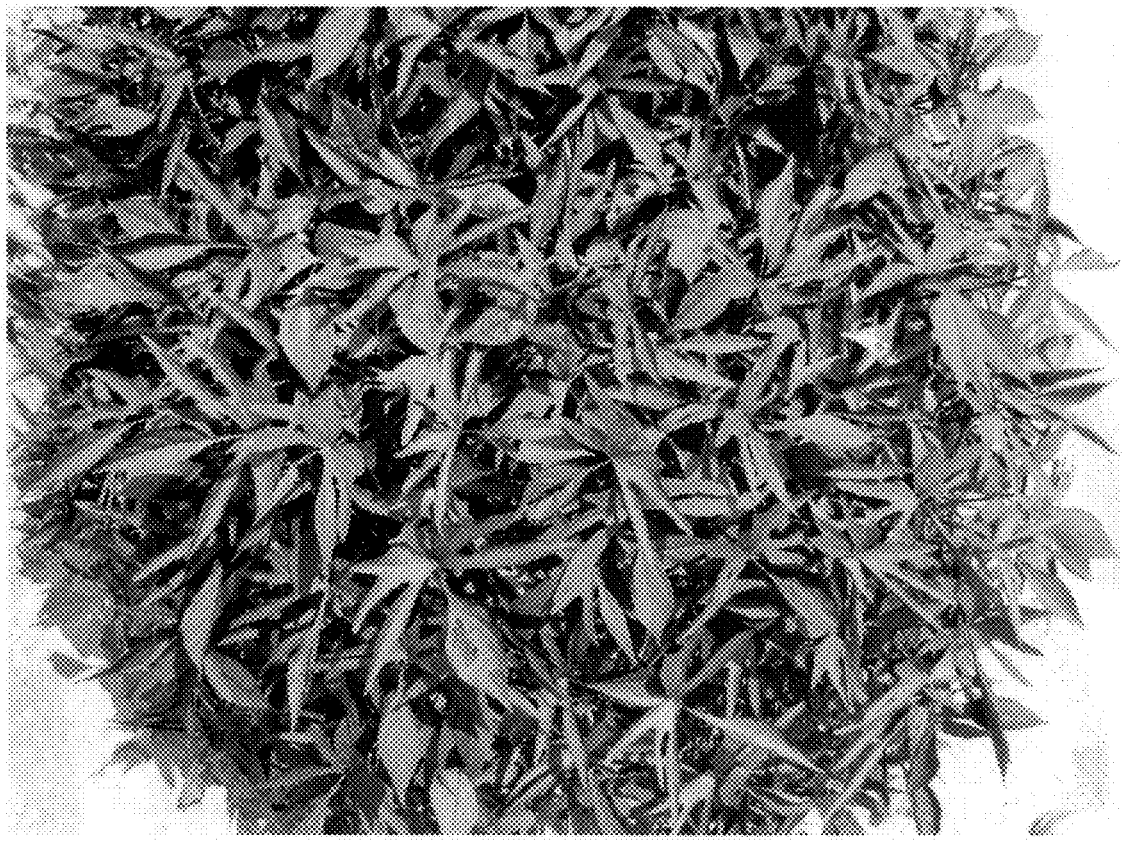
FIG. 4 shows a typical specimen of *Ipomoea batatas* 'NCORNSP-011MNLC' from the top in the field, 59 days after planting.

Above-ground structure and coloration: FIGS. 1 to 4 show the shape and coloration of a typical specimen of 'NCORNSP-011MNLC'. Colors will vary somewhat due to temperature and nutrient stress, which affect the anthocyanin pigments (which give rise to the purple color). Overall, this cultivar is a very compact, semi-upright, mounded, herbaceous plant that has an average height of 32.7 cm and an average area of spread of 58.7 cm. The growth habit of this plant is to grow upright with shoots growing outward.

Branches:

*Branching habit.*—Freely-branching with about 14 lateral branches coming off the stem; no pinching required to stimulate branching.

*Stem.*—Appearance: Round and glabrous. Aspect: Outward and upward bending. Strength: Very strong, slightly flexible, non-brittle strength. Color: RHS N77A (Dark purple). Length: About 26 cm. Diameter: About 0.6 cm. Internodes: Are short with an average length of about 1.3 cm; many lateral branches are formed and each axil has latent shoots.

*New shoots.*—Appearance: Glabrous. Aspect: Undulating. Color: RHS 143A (green) with heavy flushing near RHS N77A (purple). At approximately 1 cm of growth, shoots are entirely colored RHS N77A (purple).

*Vegetative secondary lateral branches.*—Length: About 21.1 cm. Diameter: About 0.3 cm. Internodes: Are short with an average length of about 0.6 cm; many lateral branches are formed and each axil has latent shoots. Color: RHS N186B (Dark purple).

*Petiole.*—Length: About 14.5 cm. Diameter: About 0.3 cm. Color: RHS N79A (Purple).

Foliage (leaves):

*Appearance and arrangement.*—Very dense foliage with a matte finish; leaves are alternate and simple and tend to spiral around the stem; leaves are extremely divided into 5 to 7 lobes.

*Shape.*—Broadly to narrowly linear and somewhat variable as is size.

*Quantity.*—About 5 to 7 leaves per lateral branch.

*Mature leaf.*—Length: About 14.5 cm. Width: About 16.4 cm. Lobes: Central lobe shape: Narrowly oblanceolate. Central lobe length: About 10.5 cm. Central lobe width: About 3.0 cm. Mid-vein lobe length: About 7.5 cm. Mid-vein lobe width: About 1.3 cm. Two axillary lobes: Bipartite, one long, linear lobe, one broadly oblanceolate.

*Apex.*—Acuminate.

*Base.*—Cordate.

*Margin.*—Entire.

*Texture upper surface.*—Glabrous.

*Texture lower surface.*—Glabrous.

*Venation pattern.*—Palmate at the base with arcuate veins in the center lamina.

*Color* (*of mature and immature leaves and venation*).—Table 1 shows that the leaves go from green to purple as they mature.

TABLE 1

Color of Foliage and Venation

| Leaf Structure | Upper Surface | Lower Surface |
|---|---|---|
| Immature Leaf | RHS N186B (Purple) with basal flushing RHS 137B (Green) | RHS137C (Green) with apical flushing RHS N186C (Purple) |
| Mature Leaf | RHS 147A (Yellow-green) and RHS N186B (Purple) | RHS 147A (Yellow-green) and RHS N79A (Purple) |
| Vein-mature leaf | RHS N79A (Purple) | RHS N79B (Purple) |
| Vein-immature leaf | RHS N79A (Purple) | RHS N79B (Purple) |

Flowers:

*General.*—Flowers rarely occur and if so only under short day conditions. The precise photoperiod for flower induction is currently unknown. When flowering does occur there is some variation in flower size and color, depending on the environmental conditions.

*Type and arrangement.*—Solitary, regular funnelform flowers arising from leaf axils on secondary lateral branches are formed.

*Lastingness of flowers on the plant.*—When flowers do occur, they remain open for a period of 4-6 hours, beginning at daybreak and dependant on day-length and temperature.

*Fragrance.*—Slight.

*Buds.*—Shape: Elliptic to lanceolate. Width: About 0.5 cm. Length: About 1.7 cm. Color: RHS N79A (purple).

*Corolla.*—General: Composed of 5 fused petals which form a funnel with a pentagonal limb. Width: About 4.0 cm. Length: About 4.0 cm. Throat (tube): Outer throat: RHS 77B (lavender). Inner throat: RHS 77A (purple). Petals: Fused to form a funnel shaped corolla with a pentagonal limb. Color, upper surface: RHS 77A (purple) fading to RHS 76A (lavender). Color, lower surface: RHS 77B (lavender) fading to RHS 76A (lavender). Limb color: RHS 76A (Light lavender). Limb shape: Pentagonal.

*Sepals.*—Quantity per flower: 5. General: The two outer sepals are shorter than three the inner sepals. Shape: The sepals are lanceolate and obovate. Apex: Acute. Length: About 1.0 cm. Width: About 0.3 cm. Color: Upper surface: RHS 59A (purple). Lower surface: RHS 59B (purple).

*Peduncle.*—Color: RHS 59A (purple). Length: About 9.5 cm. Diameter: About 0.3 cm.

Reproductive organs: Descriptions are based on: CIP, AVRDC, IBPGR. 1991. Descriptors for Sweet Potato. Huaman, Z., editor. International Board for Plant Genetic Resources, Rome, Italy.

*Stigma.*—Color: RHS 155C (white). Placement: Is exerted relative to the stamens. Length: About 1.9 cm. Width: About 0.1 cm.

*Style color.*—RHS 155C (white).

*Ovary.*—Superior with two locules that contain one or two ovules. At the base of the ovary there are basal glands containing nectar continuing halfway up the ovary. Ovary color: RHS 2D (yellow). Basal gland color: RHS 15A (orange).

*Stamen.*—Quantity per flower: 5. Anther length: About 0.2 cm. Anther color: RHS N155B (light pink). Pollen production: moderate. Pollen color: RHS N155D (light pink).

Disease or pest resistance: 'NCORNSP-011MNLC' is susceptible to Sweetpotato Feathery Mottle Virus and damage by Japanese beetles. Resistance or susceptibility to other known insects and pathogens of sweetpotato is unknown.

Storage root coloration: Plants form no, to very small, underground storage roots that are highly malformed and do not meet USDA Sweetpotato Storage Root Grade Standards.

Storage roots that do form typically possess RHS N186C (Dark burgundy) colored skin with RHS 157A to RHS 157B (Cream colored) flesh.

COMPARISON WITH PARENTAL LINE AND KNOWN VARIETIES

No comparison between 'NCORNSP-011MNLC' and the female parent 'NC1650-009N' is available because this parental line is no longer available.

'NCORNSP-011MNLC' is very distinct based on leaf color, leaf shape, and plant architecture. 'NCORNSP-011MNLC' is best compared with the commercial sweetpotato variety 'Sweet Caroline Purple' (U.S. Plant Pat. No. 14,912). Table 2 shows differences between 'NCORNSP-011MNLC' and 'Sweet Caroline Purple'.

TABLE 2

| Characteristic | 'NCORNSP- 011MNLC' | 'Sweet Caroline Purple' |
|---|---|---|
| Plant habit | Very compact, semi-upright | Moderately compact |
| Foliage color, upper surface | RHS 147A (Yellow-green) and RHS N186B (Purple) | RHS 187A (Purple) |
| Leaf size | Length is 14.5 cm and width is 16.4 cm | Length is 9.3 cm and width is 9.2 cm |
| Lobation | 5 to 7 very deep lobes per leaf | 3 to 5 deep lobes per leaf |

We claim:

1. A new and distinct cultivar of *Ipomoea batatas* plant named 'NCORNSP-011MNLC', substantially as illustrated and described herein.

* * * * *